United States Patent

Jenni

[11] Patent Number: 6,041,662
[45] Date of Patent: Mar. 28, 2000

[54] PROCESS AND APPARATUS FOR THE DETERMINATION OF TRUE AVERAGE PEAK VELOCITY

[75] Inventor: Rolf Jenni, Zurich, Switzerland

[73] Assignee: Endosonics Corporation, Rancho Cordova, Calif.

[21] Appl. No.: 08/923,579

[22] Filed: Sep. 4, 1997

[30] Foreign Application Priority Data

Sep. 6, 1996 [AT] Austria ................................. 1585/96

[51] Int. Cl.⁷ ............................................. G01F 1/66
[52] U.S. Cl. ............................................. 73/861.25
[58] Field of Search .................... 73/861.25; 600/454, 600/463, 464, 465, 466, 467, 468

[56] References Cited

U.S. PATENT DOCUMENTS

| | | | |
|---|---|---|---|
| 4,142,412 | 3/1979 | McLeod et al. | 73/861.25 |
| 4,259,870 | 4/1981 | McLeod et al. | 73/861.25 |
| 4,807,636 | 2/1989 | Skidmore et al. | 73/861.25 |
| 4,967,753 | 11/1990 | Hasse et al. | 128/662.06 |
| 5,052,395 | 10/1991 | Burton et al. | 128/661.09 |
| 5,105,818 | 4/1992 | Christian et al. | 128/662.06 |
| 5,271,404 | 12/1993 | Corl et al. | 128/61.08 |
| 5,443,071 | 8/1995 | Banjanin et al. | 73/861.25 |

*Primary Examiner*—Richard Chilcot
*Assistant Examiner*—Jewel V. Thompson
*Attorney, Agent, or Firm*—Flehr Hohbach Test Albritton & Herbert LLP

[57] ABSTRACT

A procedure for the determination of the true average peak velocity of particulate laden liquids in a tube, by the use of a Doppler ultrasonic transducer inserted in said tube. The average peak velocity (APV) and the null and first moment (M0 or M1) of the entire spectrum are obtained. The measured correlation between the null or first moment (M0 or M1) and APV are compared with a corresponding standard value which represents the correlation between M0 or M1 and APV upon optimal positioning of the Doppler ultrasonic transducer whereby where there is a deviation from the standard value, the transducer is moved until the values coincide.

3 Claims, 3 Drawing Sheets

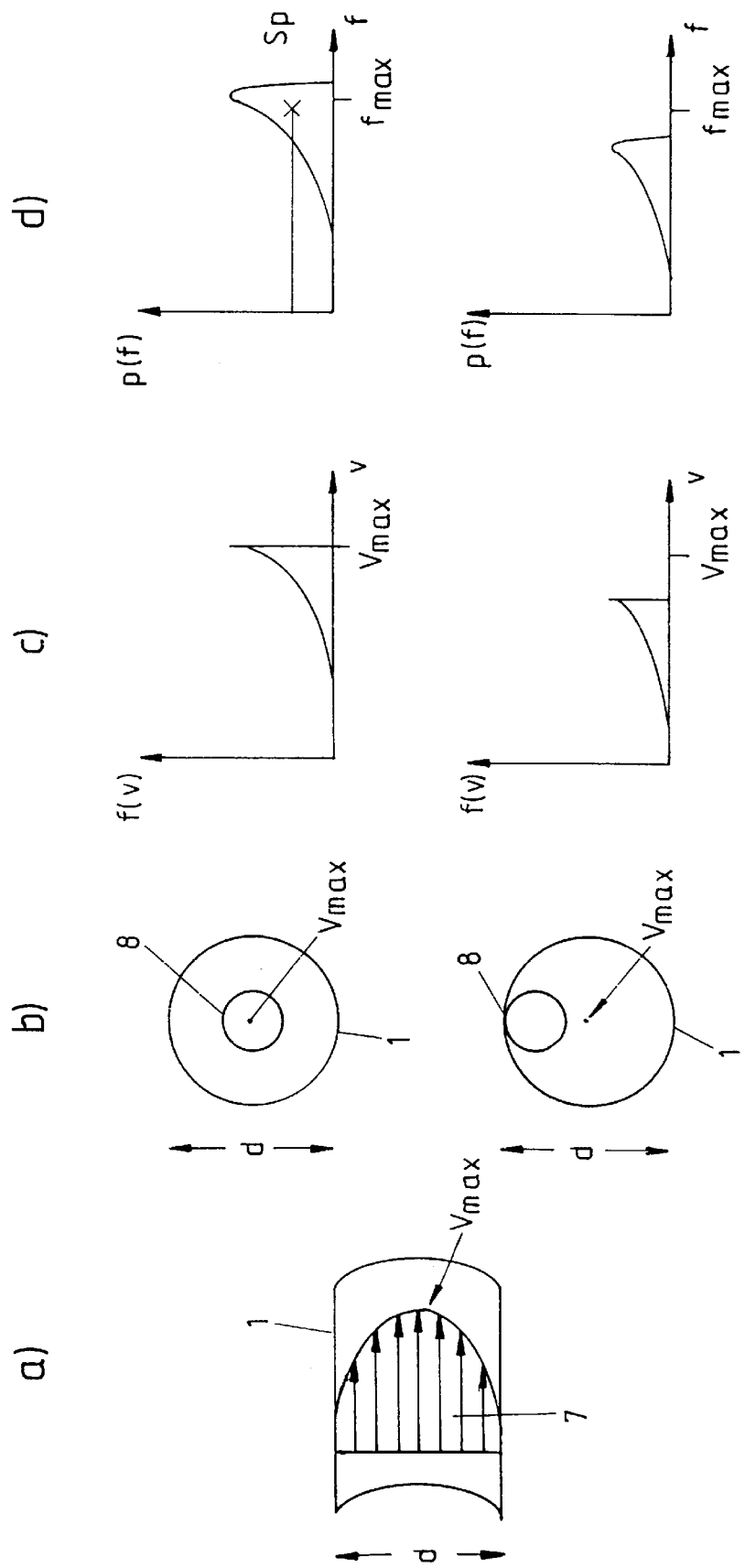

PROCESS AND APPARATUS FOR THE DETERMINATION OF TRUE AVERAGE PEAK VELOCITY

The invention concerns a procedure for the determination of the true average peak velocity of particulate laden liquid streams in a tube by means of a Doppler Ultrasonic Transducer inserted in the tube, whereby the average peak velocity (APV) and the null or first moment (M0 or M1) of the capacity spectrum is determined, therein characterized in that the measured correlation between (M0 or M1) and a corresponding standard value is compared with a straight line (5) (see FIG. 3), which represents the correlation between (M0 and M1) and APV during an optimal positioning of the Doppler Ultrasonic Transducer, whereby a deviation of the values of the transducer is brought into such a situation that the values agree.

The invention concerns a procedure and an apparatus for the determination of the true average peak velocity of a particulate laden liquid in a tube, preferably a tube with a small diameter, such as less than 6 mm, by the use of a Doppler Ultrasonic Transducer inserted in said tube, whereby the average peak velocity (APV) and the null moment or the first moment (M0 or M1, respectively) of the capacity spectrum is obtained.

Known apparatuses have already been put in service to present a signal for the formation of a spectrogram, which assumes the form of a two dimensional gray scale presentation wherein the abscissae show the time and the ordinates the frequency, and further the gray tone of a point indicates the amplitude of the corresponding frequency component at a given time. In order to form a momentary frequency spectrum, circumscribing the incremental spectrogram, it was necessary that expert services interpret the spectrogram and manually draw said circumscription, which is defined by the highest frequency at each point of time, which shows a significant amplitude greater than the background noise level. The process was tiresome and always somewhat subjective. Considering this, the invention has the purpose of creating a procedure and an apparatus, which performs this circumscription without manual intervention.

There are several apparatuses made known, which provide computerized calculations for the determination of instantaneous peak frequency groupings in a spectrogram. However, in carrying this out, many problems and disadvantages come to light. One problem is found in that the computations are very complicated and for this reason, take too long to execute in order to bring about a real time determination of the circumscribed grouping. Another problem in this procedure is that the computations in regard to the spectrum separations or amplitudes were very sensitive. Further difficulties lay in that the apparatuses were sensitive to interference signals, which can well be present in a spectrogram. In addition, responsiveness to random chronological noise levels has been noted.

There is therefore a need for a process and apparatus for the determination of true average peak velocity which overcomes the above-identified difficulties.

FIG. 4a is a partial side elevational view of a tube showing flow velocities in the tube.

FIG. 4b shows upper and lower cross sectional views of the tube shown in FIG. 4a showing the cone of the ultrasonic beam in the upper view capturing the flow velocity in the tube and in the lower view failing to capture the flow velocity in the tube.

FIG. 4c and 4d show the corresponding graphs for the velocity apportionment and the entire spectrum.

In accordance with the present invention, the above identified deficiencies have been avoided by an apparatus and a measurement method in accord with U.S. Pat. No. 5,271,404 (Cardiometrics, Inc.), which operates in accord with a process therein described.

Figure 1:
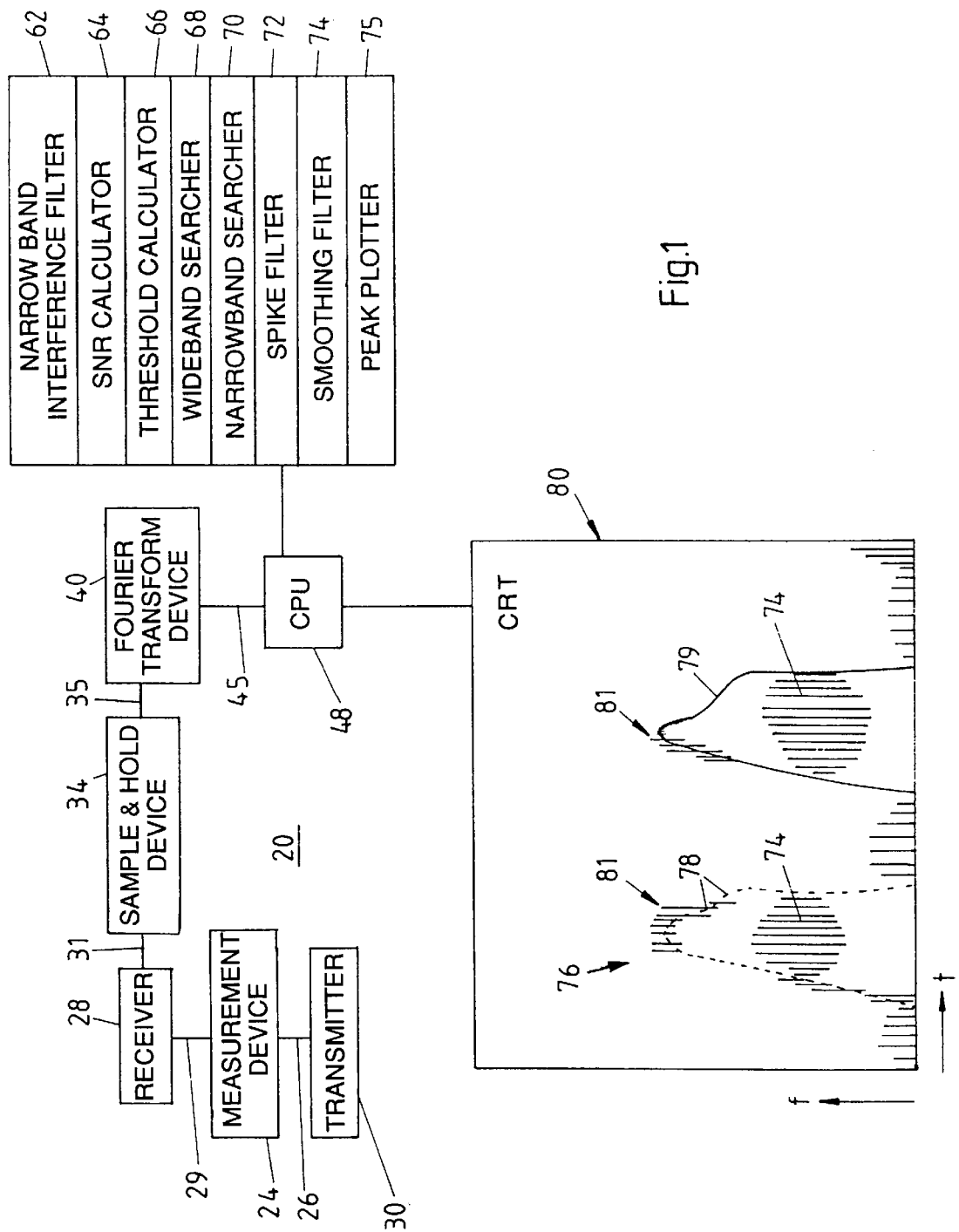
FIG. 1 is a block diagram of apparatus incorporating the present invention for carrying out the procedure of the present invention.

FIG. 1 shows in block diagram fashion an apparatus for the carrying out of this procedure. The sketch encompasses a display device 80 (see FIG. 1) with the presentation of a spectrogram 76 and the circumscribing lines which are formed by the described process. The liquid in the following example is blood with corpuscles being the particulate, and the tube is a blood vessel.

The apparatus 20, which the mentioned invention includes, is employed to the purpose of measuring and evaluating the Doppler displacement of ultrasonic signals, which signals arise from reflection from moving corpuscles within the blood vessel. In this way, a spectrum is produced on which basis, the circumscribed lines 74 are sequentially computed. The apparatus includes a measurement device 24, which gives out a signal variable with time, for instance, by a lead wire with a Doppler ultrasonic transducer mounted thereon for the measurement of the flow velocity of the blood in a human blood vessel, as is made manifest in U.S. Pat. No. 4,967,753 (Cardiometrics, Inc.). With the assumption, that the measuring device 24 is a Doppler ultrasonic transducer, the composite instrumentation 20 includes further a transmitter 30 which sends, at given repetitive times, RF impulses over the connection 26 to the measurement device 24, which device 24 also emits ultrasonic signals. The measuring device 24 receives the reflected ultrasonic signals reflected from the particulate and the receiver 28 receives the produced RF signal over the line connection 29. The signals accepted by receiver 28 vary in regard to frequency and amplitude as time progresses. The preferred manner would have the ultrasonic signal of the Doppler transducer emitted in a forward direction, in order to have a relatively broadly distributed ultrasonic beam produced, which beam would cover the greatest portion of the vessel cross-section. A 3 dB one way beam width of 20 to 90° is preferred. A broad beam, which covers the entire, or the greatest portion of the vessel cross-section, should bring such a reaction, that the Doppler-spectrum, measured peak frequency represents by far the highest flow velocity within the tube (blood vessel) and, indeed, independent of the exact orientation of the transducer.

The time varying signal [from the receiver 28] is conducted by the connecting line 31 to a measurement data memory storage 34. From that point, the accumulated signals are sent to a Fourier transforming means 40, which is preferably a digital signal, data processor dedicated to this purpose. A brief packet of the accumulated, time variable signals are thus sent from the memory storage 34 through the connection line 35 and subjected to a Fourier transformation in order to generate a frequency spectrum of said packet of the accumulated, time variable signal. A sequence of spectra are evoked continually, as the corresponding short packets of the received time variable signals come in on connection 35 and are subjected to the Fourier transformation.

The frequency spectrum can be produced in a suitable sequencing of, for instance, 100 spectral lines/second. For instance, a frequency spectrum embraces 256 frequency values (corresponding to the "Y" values on the spectrograph).

Each frequency level contains a cumulative value, which represents the corresponding frequency component of the associated packet of the time variable signal in the conducting line 35.

The spectrum produced by the Fourier transformation means 40 is conducted to a CPU 48, in order to process the spectrum data. The CPU 48 can be a conventional computer, such as, for instance, an Intel 80286. The CPU 48 operates with a command set for the processing of the sequence of spectra as fed through the conductor 45. The CPU 45 further is possessed of a memory bank with which it can function with a storage card, ROM, RAM, diskette or combinations thereof In order, each spectrum is so processed, that peak frequency value is identified, which exhibits a significant amplitude above the background noise level. The difficulty in identification of the peak frequency results from a number of factors, such as, for instance: the time variable background noise level, electrical interference signals, and transient noise peaks. In addition, the peak frequency within the spectrum must be determined within that span of time before the next spectrum is sent in, so that a momentary peak frequency circumscription can be achieved.

The circumscription means which produces line 79 and the velocity spectrogram 76 are presented by means of the cathode ray screen 80. Each vertical line of the velocity spectrogram represents a single spectrum, which, in turn, represents a short packet of the chronologically variable signal. The horizontal axis of the velocity spectrograph exhibits the time, while the vertical axis shows velocity (or in equivalent manner, the frequency). A gray scale can now be employed, in order to show the spectral strength (gray shading) of every velocity component at any time. In this way, FIG. 1 shows a darker shading in the case of the middle frequencies of each spectrum (74).

The momentary spectrum peak velocity (APV) for a sequential run of spectra is shown in the display of the velocity spectrogram 76 by means of a line of successive dots 78. It is to be noted, that the spectrum values above the background noise threshold appear regularly in the case of the velocities (see 81) higher than the true momentary spectrum velocities which can be attributed to the flow of blood and which are outlined by dots. In processes which do not conform to the present invention, the spectrum values above the true peak velocity disturb the value of the true peak velocities. The dots of the velocity peaks can be connected to one another in the formation of the circumscribing line 79, from which the true momentary spectrum peak velocity wave form arises. While the velocity spectrogram 76 is in fact expressed in frequency values, each frequency value can be easily converted into a corresponding velocity.

Figure 2:
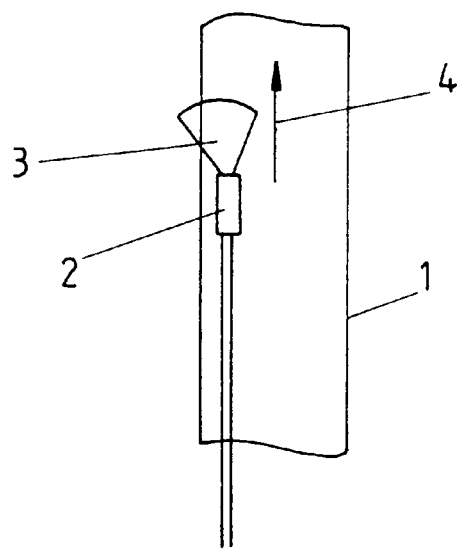
FIG. 2 is a schematic illustration of a liquid stream having a Doppler ultrasonic transducer disposed therein.

The present invention faces the problem that with the inserted Doppler Ultrasonic Transducer as a probe, no certainty exists as to whether the probe lies so disposed in the tube, that the relevant maximum velocity of the suspended particles (corpuscles) in the liquid stream is indeed being captured by the ultrasonic beam. As is to be inferred from FIG. 2, the Doppler ultrasonic transducer 2 can be so disposed, that the measured zone 3 lies outside of the maximum velocity of the particles. In this case, a false value will be given for the APV.

On this account, an indicator is desired to show if the probe demonstrates the correct value, in other words, if the probe lies properly in the tube.

Figure 3:
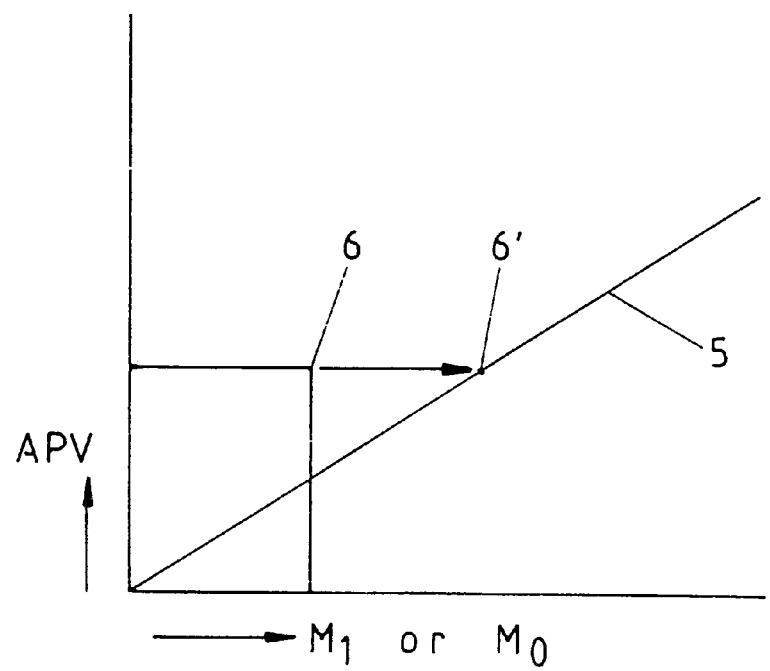
FIG. 3 is a graph showing M1 or M0 on the abscissa compared with the APV on the ordinate.

The procedure in accord with the invention is therein characterized in that the measured correlation between the null or the first moment (M0 or M-1) and APV is compared with a corresponding standard value on a straight line (5) [see FIG. 3], which line represents the correlation between M0 or M1 and APV upon optimum positioning of the Doppler ultrasonic transducer. Whereby any deviation from the value given by the transducer is brought into such a reference mode that the values [can be made to] coincide.

The apparatus in accord with the invention is therein characterized in that an indicating device to show difference between the measured correlation of APV and M0 or M1 against a standard value (line 5) is provided. The standard value of the correlation represents the optimal positioning of the Doppler ultra sonic transducer.

The apparatus is further characterized by a feature in which the standard value is depicted on a display screen as line 5.

As is explained in the introductory passages, the ultrasonic waves are reflected from the particles which move in various velocities in the fluid. These reflected waves are captured by the Doppler ultrasonic transducer and evaluated. The Doppler signal is divided up into frequency components by Fourier analysis, wherein the strength of each component is proportional to the number of the reflecting particles, which move with the corresponding velocity. In the spectrogram of FIG. 1, this represents the gray value of the spectrum. If the beam of the Doppler ultrasonic transducer covers the entire cross section of the tube, then the entire Doppler spectrum represents the velocity apportionment and the true average peak velocity is measured.

If however—which is the case with tubing of greater cross-sectional area—the ultra sonic beam does not cover the entire cross-section of the tube, then the entire spectrum shows only the apportioned velocity within this limited flow channel. If, again, the fastest moving portion of the stream is not found within this limited channel, a faulty measurement is incurred Surprisingly, evidence shows that one of the spectrum moments can be employed to serve as a position indicator. In this matter, M0 and M1 are defined as follows:

$$M0 = \int p(f) \cdot df \quad M1 = \int f \cdot p(f) \cdot df$$

wherein "p(f)" is designated as the entire spectrum and "f" is the frequency of the Doppler signal. [0 and 1 are ordinal numerals, representing zero (null) and the first order.]

In accordance with the present invention, the null or the first moment is transmitted through the entire spectrum and this value will be compared with a standard value, which is dependent upon the equipment being used. If the measured value does not agree with the standard, a faulty measurement is indicated and the transducer will have to be moved within the tube for as long as it takes the values to coincide.

In FIG. 3 is a diagram, in which the ordinate represents the APV and the abscissa shows M1 or M0. The position of the straight line 5 is dependent upon the measurement conditions and is determined by trials. This straight line 5 contains the value for the optimum positioning of the head [of the inserted probe] independently of the tube cross section.

Further on FIG. 3, a measured value 6 has been plotted in, which lies far aside from the line 5, thus exhibiting that the measured value cannot be correct. Thus, it is necessary to move the Doppler ultrasonic transducer 2 mechanically, until the measure value approaches the optimal positioning on line 5.

It is important, that the relationship between APV and M1 or M0, upon optimum positioning, shows no dependency on the diameter of the tube. In the case of the System FloWire, used for the testing, the firm Cardiometric proceeded from the standpoint that the tube diameter of 6 mm was not overstepped.

Where FIG. 4 is concerned, the invention is once more described in detail. FIG. 4a shows a longitudinal, profile section of the tube 1 with the diameter d along with the profile 7 of the flow velocity. $V_{max}$ lies in the center of the tube. FIG. 4b shows the tube 1 in cross-section, wherein the cone 8 of the beam of the Doppler ultrasonic transducer captures $V_{max}$, but fails to capture in the presentation below. Next to these, FIG. 4c and 4d show the concurrent corresponding graphs for the velocity apportionment f(v) and the entire spectrum p(f). The desired positioning in accord with the upper row of the presentations yields as d), a curve which contains $f_{max}$. The moment M1 is represented by the drawn-in key point Sp in the area lying under the curve. From the drawing presented below this, this point would lie at a different place, distant from the line 5 of FIG. 3.

In the test runs, a particulate laden liquid (blood) was pumped from a reservoir by means of a squeeze pump through four straight silicone tubes in series with known differing diameters. A Doppler ultrasonic transducer was inserted into the tubes and its position was at times changed, whereby with the apparatus in accord with FIG. 1 measurements were taken. The flow rates lay between 18 and 380 ml/min.

The optimal position of the probe was always that position with the maximum average peak velocity (APV) and first moment M1 at a given flow rate. At the optimal position, the APV lay between 17 and 83 cm/sec in all the different tubes, while the corresponding value for M1 was found between 19 and 135 units. The correlation between APV and M1, at optimal positioning of the probe was practically equal and ran APV=12.1+0.54 M1, independently of the tube diameter. The line 5 in FIG. 3 represents this correlation.

I claim:

1. A procedure for the determination of the true average peak velocity of particulate laden liquids in a tube by the use of a Doppler ultrasonic transducer inserted in said tube whereby the average peak velocity (APV) and the null and first moment (M0 or M1) of a spectrum are obtained comprising the steps of:

comparing the measured correlation between the null or first moment (M0 or M1) and APV with a corresponding standard value which represents the correlation between M0 or M1 and APV upon optimal positioning of the Doppler ultrasonic transducer; and moving the transducer when there is a deviation from the standard value until the values coincide.

2. An apparatus as defined in claim 1 further comprising a display device for the visual presentation of the difference between the measured correlation APV and M1 or M0 and a standard value, whereby the standard value of the correlation represents the optimal positioning of the Doppler ultrasonic transducer.

3. An apparatus as in claim 2 wherein the standard value is depicted on a display screen.

* * * * *